United States Patent [19]

Markel et al.

[11] Patent Number: 5,053,004
[45] Date of Patent: Oct. 1, 1991

[54] CATHETER HAVING TWO COAXIAL LUMENS

[75] Inventors: David F. Markel, Collegeville; Anthony J. Madison, Harleysville; David E. Roberts, Zieglersville; William R. Harkins, Norristown, all of Pa.

[73] Assignee: Medical Components, Inc., Harleysville, Pa.

[21] Appl. No.: 571,930

[22] Filed: Aug. 24, 1990

[51] Int. Cl.⁵ .................. A61M 25/00; B23P 11/00
[52] U.S. Cl. ................................ 604/43; 29/428
[58] Field of Search ............ 604/43, 44, 45; 29/428

[56] References Cited

U.S. PATENT DOCUMENTS

| | | | |
|---|---|---|---|
| 1,696,018 | 12/1928 | Schellberg | 604/43 |
| 2,564,977 | 8/1951 | Hu | 604/44 X |
| 3,528,427 | 9/1970 | Sheridan | 604/45 |
| 3,771,527 | 11/1973 | Ruisi | 604/43 |
| 3,863,632 | 2/1975 | Schwartz | 604/44 |
| 3,875,938 | 4/1975 | Mellor | 604/44 |
| 4,037,599 | 7/1977 | Raulerson | 604/44 |
| 4,096,860 | 6/1978 | McLaughlin | 604/44 |
| 4,099,528 | 7/1978 | Sorenson | 604/44 |
| 4,134,402 | 1/1979 | Mahurkar | 604/44 |
| 4,202,332 | 5/1980 | Tersteegen | 604/44 |
| 4,217,895 | 8/1980 | Sagae | 604/44 |
| 4,270,535 | 6/1981 | Bogue | 604/44 |
| 4,493,696 | 1/1985 | Uldall | 604/43 |
| 4,583,968 | 4/1986 | Mahurkar | 604/43 |
| 4,692,141 | 9/1987 | Mahurkar | 604/43 |

Primary Examiner—William H. Grieb
Attorney, Agent, or Firm—William H. Eilberg

[57] ABSTRACT

A double-lumen catheter is made of two generally coaxial tubes. The tubes are joined, at their distal ends, by a sleeve inserted between the tubes, the sleeve being bonded to both tubes. The inner and outer tubes are connected, respectively, at their proximal ends, to first and second hubs. The hubs are bonded together. The distal ends of the tubes may be formed into a tapered tip, preferably having a rounded edge. The proximal ends of the tubes can be connected to external fluid devices. The invention also includes a method of making the catheter. According to this method, inner and outer tubes are separately formed, and the proximal end of each tube is connected to a hub. Then, the inner tube is threaded into the outer tube, until the distal ends of the tubes are near each other. A sleeve is inserted between the tubes, at the distal end, and the sleeve is then bonded to both tubes. The hubs are also bonded together. Thus, the tubes are firmly joined to each other, but only at their distal and proximal ends. The outer tube has a plurality of holes, located around its circumference, at the distal end, to provide access to the outer lumen. The distal tip provides an exit port for the inner lumen. The catheter can also be provided with a dilator/stylet which is initially inserted within the inner lumen, and which is withdrawn after the catheter has been inserted into a patient.

31 Claims, 3 Drawing Sheets

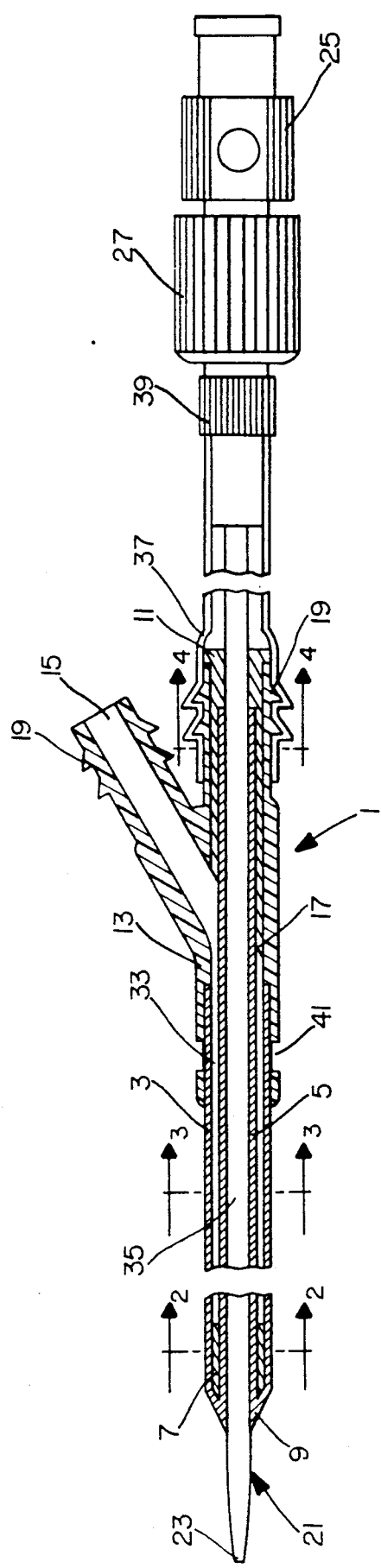
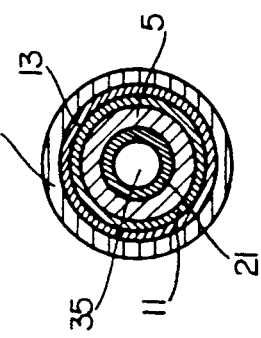
FIG. 4
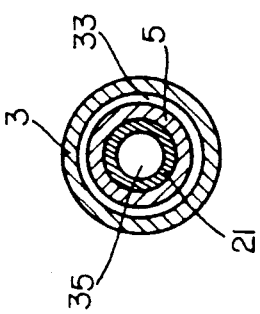
FIG. 3
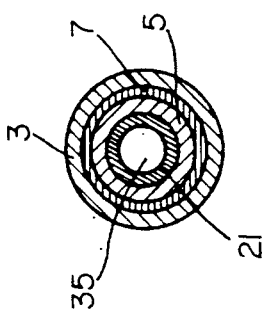
FIG. 2
FIG. 1

CATHETER HAVING TWO COAXIAL LUMENS

BACKGROUND OF THE INVENTION

This invention relates to the field of catheters, especially catheters used for hemodialysis. In particular, the invention concerns a double-lumen catheter in which the lumens are disposed coaxially.

Double-lumen catheters for hemodialysis, and for other purposes, have been known for a long time. Some of these catheters have had coaxial lumens, as exemplified by U.S. Pat. Nos. 4,493,696, 4,099,528, 4,270,535, and 4,202,332. Other catheters of the prior art have had lumens with a D-shaped cross-section, with a planar septum separating the lumens. Examples of the latter structure are given in U.S. Pat. Nos. 4,134,402, 4,583,968, and 4,692,141.

For a given pressure, the rate of fluid flow, through a lumen of circular cross-section, is greater than the flow rate for a lumen of D-shaped cross-section of comparable area. Not only does the circular cross-section generate less turbulence, but the back pressure developed is also less, so that less force is required to push a given volume of fluid through the catheter. Moreover, a circular cross-section enjoys the advantage that it does not have internal crevices which can promote the formation of blood clots.

A lumen having an annular cross-section enjoys substantially the same advantages possessed by circular lumens. Like the circular cross-section, an annular cross-section also does not have sharp bends, corners, or crevices.

Because of the inherent advantages of lumens having circular cross-sections, many attempts have been made to develop a practical catheter having coaxial lumens. These attempts have not been entirely successful, for the reasons explained below.

One major problem with the coaxial catheters of the prior art is that they have had no acceptable means of connecting the inner tube to the outer tube at the distal end. Indeed, in many of the double-lumen coaxial catheters of the prior art, the distal end of the inner tube simply dangles within the outer tube, and is not anchored at all. Each time such a catheter is used, it is necessary to insert the inner tube into the outer tube. The inner tube must be withdrawn upon completion of a dialysis operation. This procedure of repeatedly inserting and withdrawing the inner tube is extremely cumbersome, since it is necessary, in effect, to dismantle the catheter after each dialysis operation. The procedure is also relatively expensive, because it is necessary to replace the inner tube each time one wants to use the catheter again. Thus, if one uses a single catheter to perform 20 dialysis operations, it is necessary to discard an inner tube 20 times, during the life of the catheter.

Another disadvantage of coaxial catheters of the prior art is their tendency to cause blockage of the outer lumen. Due to fluid flow into the catheter, an area of vacuum is likely to develop. If the inner tube is dangling freely within the outer tube, at its distal end, the inner tube may be pulled, due to the vacuum, towards the interior wall of the outer tube. The inner tube may thus block one or more of the holes providing access to the outer lumen, thereby reducing or even totally blocking blood flow into that lumen.

Yet another problem with coaxial catheters of the prior art is the risk of leakage. Since the inner tube is intended to be removed and inserted periodically, it is necessary to provide a hemostasis valve, and to pass the inner tube through that valve. The presence of such a valve creates an additional risk of leakage.

The above-described problems are alleviated by non-coaxial catheter designs, such as those having lumens of D-shaped cross-sections, as shown in the above-cited U.S. Pat. Nos. 4,134,402, 4,583,968, and 4,692,141. The catheters shown in the latter patents have lumens which do not dangle at their distal ends, and which are firmly supported within the catheter. However, these catheters have the disadvantages associated with lumens of non-circular cross-sections, as described above.

The present invention solves the problems inherent in the coaxial catheters of the prior art, and provides a practical double-lumen catheter having lumens of circular and annular cross-section. The catheter of the present invention has an inner lumen which is firmly and permanently mounted within the outer lumen, thereby providing a rigid and reliable structure. The catheter of the present invention therefore enjoys the advantages associated with circular lumens, while still being both safe and economical.

SUMMARY OF THE INVENTION

The catheter of the present invention includes a generally cylindrical inner tube inserted within a generally cylindrical outer tube. The tubes are preferably formed of a thermosensitive plastic material. A generally cylindrical sleeve is inserted between the tubes, at their distal ends, and is bonded to both the inner tube and the outer tube. The distal end is preferably formed into a tip, such as a tapered tip, although the edge of the tip is preferably rounded, and is not, by itself, capable of puncturing the skin. The inner tube defines a generally cylindrical inner lumen which exits at the distal end, through the tip. The outer tube and inner tube define a generally annular outer lumen which exits through holes formed in the outer tube, also near the distal end. Because the cross-section of the outer lumen is annular, these holes can be disposed around more than half the circumference of the outer tube.

The catheter further includes hubs, affixed respectively to the exterior surfaces of the inner and outer tubes, near their proximal ends. The outer lumen hub extends beyond the proximal end of the outer tube, so that the outer lumen hub can be bonded to the inner lumen hub. Both hubs define means for connecting the lumens to external fluid devices.

The invention also includes a method of making the coaxial double-lumen catheter. According to the method, the inner and outer tubes are separately formed, and are connected to hubs at their proximal ends. A plurality of holes are punched in the outer tube, near its distal end. Then, the inner tube is threaded into the outer tube, such that the distal ends of the two tubes become aligned, or nearly aligned. A small cylindrical sleeve is inserted, at the distal end, between the two tubes, and is bonded to the tubes. The hubs are bonded to each other. The distal end may be formed into a tip, while maintaining an opening for the inner (distal) lumen.

It is therefore an object of the invention to provide a double-lumen coaxial catheter.

It is another object to increase the rate of fluid flow through a double-lumen catheter, for a given outer diameter of the catheter.

It is another object to improve the reliability of double-lumen coaxial catheters.

It is another object to provide a double-lumen coaxial catheter which can be easily inserted with a dilator.

It is another object to minimize the likelihood of blockage of lumens in a double-lumen catheter.

It is another object to provide a double-lumen catheter which minimizes the risk of blood clots.

It is another object to provide a double-lumen catheter having the advantages of circular lumens, but which is also economical to use.

It is another object to provide a method of making a double-lumen coaxial catheter.

Other objects and advantages of the invention will be apparent to those skilled in the art, from a reading of the following brief description of the drawings, the detailed description of the invention, and the appended claims.

BRIEF DESCRIPTION OF THE DRAWINGS

FIG. 1 is a partially-fragmentary, partial cross-sectional view of the double-lumen catheter of the present invention, showing, partially in full, the dilator inserted within the catheter.

FIG. 2 is a cross-sectional view of the distal end of the catheter, taken along the line 2—2 of FIG. 1.

FIG. 3 is a cross-sectional view, taken along the line 3—3 of FIG. 1.

FIG. 4 is a cross-sectional view of a portion of the proximal end of the catheter, taken along the line 4—4 of FIG. 1.

DETAILED DESCRIPTION OF THE INVENTION

Figure 5:
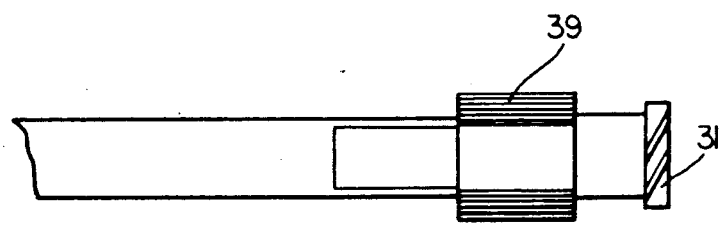
FIG. 5 is a side elevational view of the proximal end of the catheter, with the dilator removed.

FIG. 1 is a partially fragmentary cross-sectional view of the double-lumen catheter of the present invention. FIG. 1 also shows, in full, the dilator which is preferably kept within the catheter and later withdrawn after the catheter has been inserted into a patient. The dilator preferably also functions as a stylet, which acts as a stiffener for the catheter. A stylet is useful because a catheter made of soft plastic is not easily inserted by itself. In the embodiment shown, the dilator and stylet are the same item. In this specification, whenever the term "dilator" is used, it is therefore understood that the term may include a structure that also functions as a stylet.

Catheter 1 includes outer tube 3 and inner tube 5. The tubes are preferably formed of a plastic material. A preferred type of plastic, for this purpose, is pellathane, which is a heat-sensitive polyurethane. This material becomes soft whenever heat is applied, so that it becomes soft when inserted in the body. However, the catheter can be made with other materials, and the invention is not limited to a particular choice of material.

Inner tube 5 defines inner lumen 35. Outer lumen 33 is defined by inner tube 5 and outer tube 3. The lumens are independent, in the sense that fluid flowing through one lumen cannot contact the fluid flowing in the other lumen, inside the catheter. When the catheter is used for hemodialysis, the outer lumen is preferably the lumen through which blood is withdrawn from the vessel and conveyed to the dialysis machine. The inner lumen is therefore the lumen which returns purified blood to the body. The outer lumen is also known as the "arterial" lumen, and the inner lumen is known as the "venous" lumen.

A generally cylindrical sleeve 7, which can be made of the same material used to form the tubes 3 and 5, or of a different material, is inserted between the tubes, at their distal ends. The sleeve is bonded, preferably by heat sealing, to both of the tubes. The sleeve may be one or two centimeters long, but its length is not critical, and can be varied. In general, the sleeve should be long enough to create a reliable bond between the inner and outer tubes, but not so long that the exit port of the outer lumen is spaced too far from the distal end of the catheter.

The distal end of the catheter is formed into tip 9, which is shown as a tapered tip. The tip defines an opening to the outside, for inner lumen 35. The corresponding openings for outer lumen 33 comprise a plurality of holes punched in the outer tube. For convenience and clarity of illustration, these holes are not shown in FIG. 1, but instead they are specifically illustrated in FIG. 7.

Inner tube 5 is connected, at its proximal end, to inner lumen hub 11, which can be made of plastic, and which is preferably molded directly around the proximal end of the tube. Outer tube 3 is similarly connected, at its proximal end, to outer lumen hub 13. The outer lumen hub defines side port 15 which is fluidly connected to the outer lumen. The outer lumen hub extends beyond the proximal end of outer tube 3, so that a portion of the outer lumen hub is directly adjacent a portion of the inner lumen hub. The hubs are bonded together, such as by an adhesive.

The distal end of the inner lumen hub is beveled, as indicated at 17. The bevel helps to direct fluid from the outer lumen through side port 15, and prevents blood from entering a crevice, where it could clot. Also, the bevel serves to define a straight path for fluid flow into port 15, thereby minimizing turbulence.

The inner lumen hub 11 also extends beyond its associated tube, in the proximal direction. The purpose of this extension is to provide a convenient means of attachment of the inner lumen to an external fluid device (not shown) while maintaining the uniformity of the inner diameter of the inner lumen. The hub includes barbs 19 which anchor flexible extension line 37 which is attached to suitable Luer connector 39, or to some other type of connector. Connector 39 can be connected to a suitable fluid device (not shown), which does not form part of this invention.

A similar extension line can be placed over the barbs for side port 15. The extension lines, connectors, and fluid device associated with side port 15 are not shown, as they can be of any conventional design, and do not form part of the invention. Also, the proximal end of the catheter can be provided with clamps, preferably one for each lumen. The clamps are also not shown, as they are entirely conventional components, and are also not part of the invention.

Dilator 21 is shown inserted into catheter 1, in FIG. 1. The dilator comprises a tube inserted within inner tube 5. The dilator protrudes beyond the distal end of the catheter, as shown. The dilator terminates in dilator tip 23 which is tapered down sufficiently to slide easily but firmly over a guide wire (not shown). If the body of the dilator has a diameter of 4 French (i.e. about 0.060 inches), the diameter of the dilator tip may taper down to about 0.040 inches. The latter dimensions are only exemplary, and many other dimensions could have been chosen. The invention is not limited to any particular size of catheter or dilator.

The outer lumen hub is preferably formed with indentation 41. The indentation provides a space for mounting a rotating suture collar (not shown) which is a component having holes which aid in suturing the catheter to the skin of the patient. Note that, at the location of the indentation, the outer lumen hub becomes very thin, but it is still one piece. The catheter can also be made without the indentation, within the scope of the invention.

The dilator also includes rotating collar 27 which is screwed onto a threaded flange on the catheter. The threaded flange is not visible in FIG. 1, but is shown as element 31 in FIG. 5, which is a side elevational view of the proximal end of the catheter, without the dilator. Many other configurations can be used for the dilator.

FIGS. 2, 3, and 4 show cross-sections taken along the lines 2—2, 3—3, and 4—4, respectively, of FIG. 1. Similar reference numerals designate identical components in the various figures. FIGS. 2-4 all show inner lumen 35, which is defined by inner tube 5. FIG. 3 shows outer lumen 33, which is defined by outer tube 3 and inner tube 5. FIG. 3 therefore shows the generally annular cross-section of the outer lumen.

Figure 6:
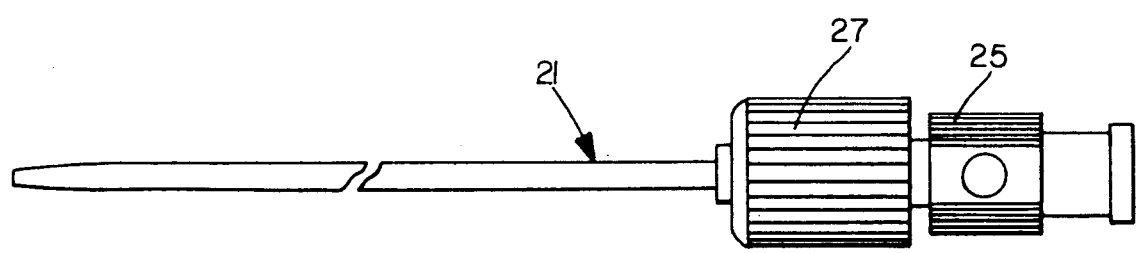
FIG. 6 is a side elevational view of the dilator which has been removed from the catheter.

FIG. 6 is a side elevational view of dilator 21 itself, as removed from the catheter. The structure of the dilator can be modified, within the scope of the invention. The dilator is intended to be threaded over a guide wire, which has first been inserted by the well-known Seldinger skin to enable the catheter to penetrate. The catheter can conveniently be stored with the dilator screwed onto it, the dilator being unscrewed and removed only after the catheter has been inserted into the patient.

It is also possible to use the catheter of the present invention without a dilator. The catheter could instead be inserted through a percutaneous sheath, or it could be formed with a tip which tapers down to the diameter of a guide wire. Such alternatives are intended to be within the scope of the invention.

Figure 7:
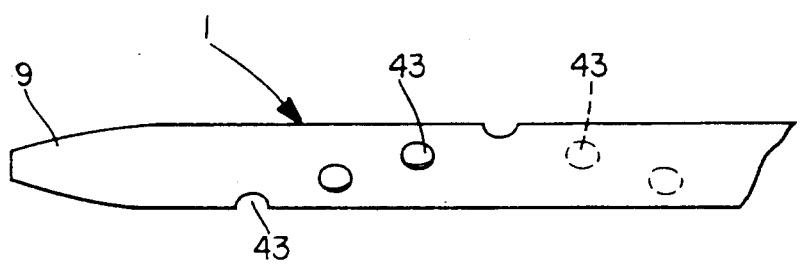
FIG. 7 is a side elevational view of a portion of the distal end of the catheter, showing holes in the outer tube disposed around the circumference of the tube.

FIG. 7 is a side elevational view of a portion of the distal end of the catheter, showing the arrangement of holes 43 in the outer tube. Because the outer lumen is annular, it is feasible to place these holes around substantially the entire circumference of the outer tube. Moreover, such an arrangement is especially desirable for preventing occlusion of the lumen. In virtually any catheter, the flow of fluid into a lumen creates a local vacuum, which causes the catheter to be sucked towards the vessel wall. If the holes providing access to the outer lumen are disposed on only one side of the outer tube, then that side of the tube may be drawn towards the vessel wall, and the lumen may therefore become blocked. This condition is an inherent disadvantage of catheters having D-shaped lumens, since the holes providing access to a particular lumen cannot be located around the entire circumference of the outer tube. With the present invention, even if one or two of the holes become blocked, the holes on the opposite side of the tube almost certainly will not be blocked. Therefore, the catheter of the present invention minimizes the likelihood of blockage of the outer lumen.

Figure 8:
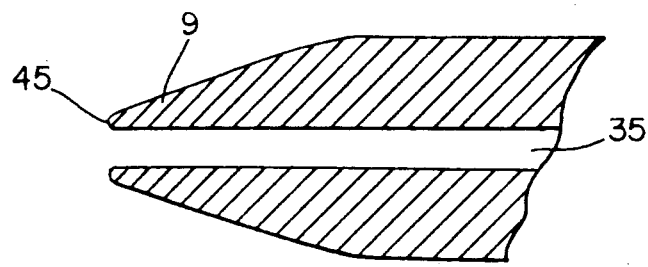
FIG. 8 is a fragmentary cross-sectional view of the distal tip of the catheter, showing the rounded edge of the tip.

FIG. 8 is a fragmentary cross-sectional view of distal tip 9 of the catheter of the present invention. As shown in FIG. 8, the edge 45 of the distal end is rounded. Rounding of the edge tends to prevent stenosis, which is an irritation of the vessel wall. Stenosis can be harmful, because, in serious cases, the irritation can close off the vessel, due to formation of a scab. The rounded edge avoids such irritation.

Thus, in the preferred embodiment, the tip is not sharp enough to penetrate the skin by itself. Instead, as stated above, the catheter is inserted with the aid of a dilator or other introducer. Thus, the catheter can be inserted to a desired distance within the patient, without irritating the vessel walls with a sharp end.

However, if desired, the catheter tip can also be made sharp, without affecting the basic internal catheter structure described above. Many variations of tip construction are possible.

FIGS. 9a through 9f show the major steps of the method of making the coaxial double-lumen catheter of the present invention. These figures are somewhat fragmentary, as their purpose is only to illustrate the method.

Figure 9A:
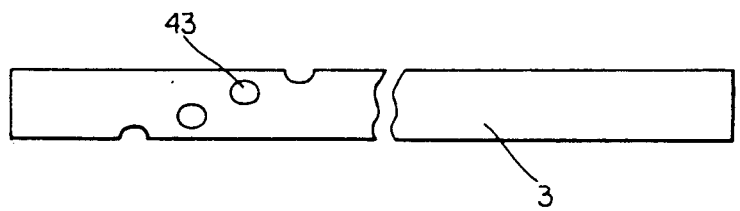
FIGS. 9a through 9f show the major steps of a method of making the double-lumen catheter of the present invention.
Figure 9B:
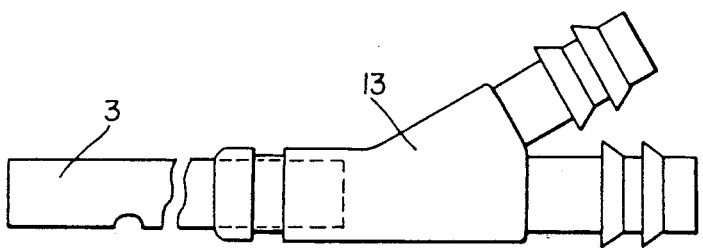

The catheter of the present invention is made as follows. First, one forms the outer tube, preferably by extrusion of plastic. One forms holes in the outer tube, near the end that will become the distal end. FIG. 9a shows outer tube 3 with holes 43. Then, one forms outer lumen hub 13 around the proximal end of the outer tube, as shown in FIG. 9b. The outer lumen hub extends beyond the proximal end of the tube. The hub is preferably molded directly onto the proximal end of the tube, so that the steps of forming the hub and bonding the hub to the tube can be done in one operation.

Figure 9C:
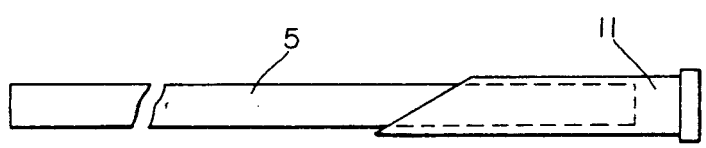

Next, inner tube 5 is formed, again preferably by extrusion. The inner lumen hub 11 is formed at one end (the proximal end) of the tube, as shown in FIG. 9c. The process of molding and bonding can be the same as used for the outer lumen hub.

Figure 9D:
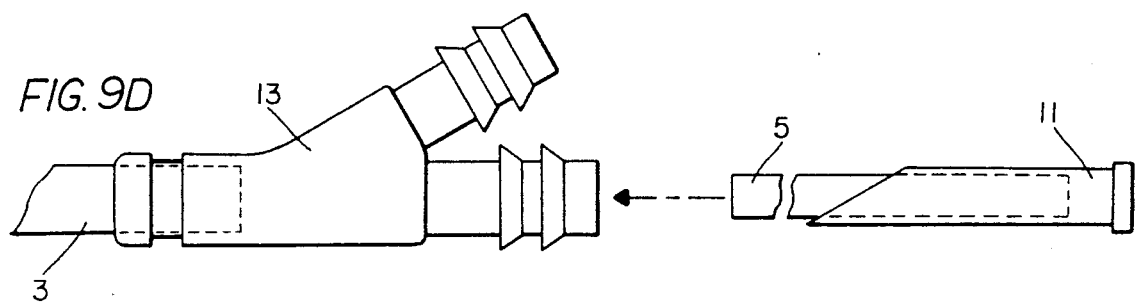

Then, the inner tube is threaded through the outer tube. As shown in FIG. 9d, inner tube 5 is inserted at the proximal end of the outer tube, and is pushed through the outer tube, towards the distal end, until the inner and outer lumen hubs are in the positions indicated in FIG. 1. The hubs are then bonded together, preferably by an adhesive.

Figure 9E:
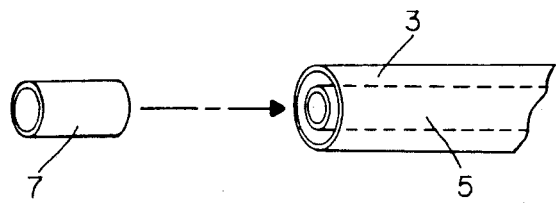
Figure 9F:
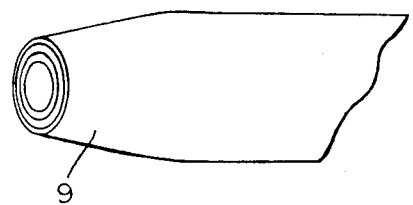

Next, plastic sleeve 7 is inserted at the distal end, between the inner and outer tubes, as shown in FIG. 9e. The sleeve may be adhesively fastened to the tubes. The distal end of the tubes is then placed in a tip molding machine (not shown) which applies heat (such as by generating a radio-frequency electromagnetic signal). The heat causes the inner and outer tubes to become fused to the sleeve, and also makes it possible to shape tip 9. The bonding of the inner and outer tubes can therefore be performed simultaneously with the shaping of the tip, or these steps can be performed separately.

The reason for using adhesive when inserting the sleeve is to hold the sleeve in place, temporarily, while the distal end is being placed in the tip molding machine. It is possible to omit the step of applying adhesive, provided that the sleeve can be kept in place, by other means, before it is fused to the tubes.

The edge of the tip can then be rounded, either by grinding it or by placing it in another heat-molding machine. The proximal end of the catheter can then be provided with conventional fittings for connection to external fluid devices.

The order of some of the steps, in the method described above, can be altered. For example, the steps of forming the tubes and hubs can be reversed, as it is not important which tube is formed first. The holes in the outer tube can be formed after the outer lumen hub has been attached to the tube. Also, it is possible to bond the distal ends of the tubes before bonding the hubs at the proximal end of the catheter. Other variations in order of the steps are possible.

As suggested above, it is also possible to form the inner and outer lumen hubs as one combined piece. In this alternative, the inner tube is first threaded into the outer tube, and the hubs are molded around both tubes, forming one piece of plastic. The tubes are joined at their distal end in the same manner as before.

While the invention has been described with respect to specific embodiments, it is understood that many variations are possible. For example, instead of molding the hubs directly around the tubes, one can separately form the hubs and connect them to the tubes. The particular fittings and connectors, at the proximal end of the catheter, as well as the fluid devices used, can be modified substantially, without affecting the essence of the invention. Different materials can be used for the tubes, the hubs, or the sleeve, and the means of bonding can also be varied. These and other variations should be considered within the spirit and scope of the following claims.

What is claimed is:

1. A double-lumen catheter, comprising:
   a) a generally cylindrical inner tube having interior and exterior surfaces,
   b) a generally cylindrical outer tube having interior and exterior surfaces, the outer tube being arranged around the inner tube such that the inner and outer tubes are substantially coaxial, the inner tube defining an inner lumen having a generally circular cross-section, the inner and outer tubes defining an outer lumen having a generally annular cross-section, the tubes having a proximal end and a distal end,
   c) a generally cylindrical sleeve inserted between the tubes at the distal end, the sleeve being bonded to the inner tube and to the outer tube,
   d) a first hub formed around the exterior surface of the proximal end of the inner tube,
   e) a second hub formed around the exterior surface of the proximal end of the outer tube, the second hub extending beyond the outer tube in the proximal direction, wherein the first and second hubs are bonded together, and
   f) means for connecting the lumens to fluid conveying devices.

2. The catheter of claim 1, wherein there are a plurality of holes in the outer tube, the holes being located near the distal end of the outer tube, the holes being disposed around more than half the circumference of the outer tube.

3. The catheter of claim 1, wherein the distal ends of the tubes define a tip, the tip including an opening fluidly connected to the first lumen.

4. The catheter of claim 3, wherein the edges of the tip are rounded.

5. The catheter of claim 1, further comprising a dilator, the dilator being inserted within the inner lumen, the catheter having means for attaching the dilator to the catheter.

6. The catheter of claim 5, wherein the attaching means comprises a threaded flange located near the proximal end of the catheter, and wherein the dilator includes threaded means for engaging said flange.

7. The catheter of claim 5, wherein the dilator comprises a generally hollow, cylindrical tube.

8. The catheter of claim 7, wherein the dilator protrudes beyond the distal ends of the inner and outer tubes.

9. The catheter of claim 1, wherein the connecting means includes a side port which is fluidly connected to the outer lumen.

10. The catheter of claim 9, wherein the first hub includes a bevel at its distal end, the bevel comprising means for directing fluid into the side port, and for preventing fluid from becoming trapped in the outer lumen, proximal of the side port.

11. A double-lumen catheter comprising a pair of generally coaxial tubes, the tubes defining independent inner and outer lumens, the tubes having distal ends and proximal ends, the tubes being joined at their distal ends by a sleeve located between the tubes, the sleeve being bonded to both of the tubes, each of the tubes being bonded, respectively, at their proximal ends, to first and second hubs, the hubs being bonded to each other.

12. The catheter of claim 11, wherein one of the tubes is the outer tube and one of the tubes is the inner tube, wherein there are a plurality of holes in the outer tube, the holes being located near the distal end of the outer tube, the holes being disposed around more than half the circumference of the outer tube.

13. The catheter of claim 11, wherein the distal ends of the tubes define a tip, the tip including an opening fluidly connected to the inner lumen.

14. The catheter of claim 13, wherein the edges of the tip are rounded.

15. The catheter of claim 11, further comprising a dilator, the dilator being inserted within the inner lumen, the catheter having means for attaching the dilator to the catheter.

16. The catheter of claim 15, wherein the attaching means comprises a threaded flange located near the proximal end of the catheter, and wherein the dilator includes threaded means for engaging said flange.

17. The catheter of claim 15, wherein the dilator comprises a generally hollow, cylindrical tube.

18. The catheter of claim 17, wherein the dilator protrudes beyond the distal ends of the inner and outer tubes.

19. The catheter of claim 11, wherein the catheter includes means for connecting the lumens to fluid conveying devices.

20. The catheter of claim 19, wherein the connecting means includes a side port which is fluidly connected to the outer lumen.

21. The catheter of claim 20, wherein one of the tubes is an inner tube and one of the tubes is an outer tube, and wherein the hub which is connected to the inner tube includes a bevel at its distal end, the bevel comprising means for directing fluid into the side port, and for preventing fluid from becoming trapped in the outer lumen, proximal of the side port.

22. A method of making a double-lumen coaxial catheter, the method comprising the steps of:

a) forming an outer tube, the outer tube having a distal end and a proximal end, the outer tube having interior and exterior surfaces, b) punching at least one hole near the distal end of the outer tube, c) attaching a hub to the exterior surface of the outer tube, near the proximal end of the outer tube, such that the hub projects beyond the outer tube, d) forming an inner tube, the inner tube having a distal end and a proximal end, the inner tube having interior and exterior surfaces, e) attaching a hub to the exterior surface of the inner tube, near the proximal end of the inner tube, f) threading the inner tube into the outer tube, such that the inner tube moves from the proximal end towards the distal end of the outer tube, until the inner tube reaches the vicinity of the distal end of the outer tube, g) inserting a generally cylindrical sleeve between the inner and outer tubes, at their distal ends, h) bonding the sleeve to both the inner and outer tubes, and i) bonding the hubs of the tubes to each other.

23. The method of claim 22, wherein step (h) also includes forming the distal ends of the tubes into a tip, the tip including means for fluidly connecting the inner tube to the outside of the catheter.

24. The method of claim 22, further comprising the step of attaching fittings to the hubs for connection of the hubs to external fluid devices.

25. The method of claim 24, further comprising the step of inserting a dilator into the inner tube, such that the dilator protrudes beyond the distal end of the inner tube.

26. The method of claim 22, wherein step (h) comprises the step of applying heat to the tubes at their distal ends, so that the sleeve becomes fused to the tubes.

27. The method of claim 26, wherein the heat-applying step is preceded by the step of adhesively fastening the sleeve to the tubes.

28. A method of making a double-lumen coaxial catheter, comprising the steps of:

a) providing an inner tube having distal and proximal ends, and having at least one hole near the distal end, b) connecting a first hub to the proximal end of the inner tube, c) providing an outer tube having distal and proximal ends, the outer tube having a diameter greater than that of the inner tube, d) connecting a second hub to the proximal end of the outer tube, e) threading the inner tube into the outer tube such that the distal end of the inner tube is positioned near the distal end of the outer tube, f) bonding the inner and outer tubes together at their distal ends, and g) bonding the first and second hubs together.

29. The method of claim 28, wherein step (f) comprises the step of inserting a sleeve between the inner and outer tubes, at their distal ends, and applying heat to the tubes at their distal ends, so that the sleeve becomes fused to the tubes.

30. The method of claim 29, wherein the heat-applying step is preceded by the step of adhesively fastening the sleeve to the tubes.

31. A method of making a double-lumen coaxial catheter, comprising the steps of:

a) providing an inner tube having distal and proximal ends, and having at least one hole near the distal end, and an outer tube having distal and proximal ends, the outer tube having a diameter greater than that of the inner tube, b) threading the inner tube into the outer tube such that the distal end of the inner tube is positioned near the distal end of the outer tube, c) connecting a hub to the proximal ends of the tubes, in such a manner that the hub comprising means for holding the inner tube within the outer tube, and d) bonding the inner and outer tubes together at their distal ends.

* * * * *